United States Patent [19]

Norinder et al.

[11] Patent Number: 5,585,404
[45] Date of Patent: Dec. 17, 1996

[54] 3,5,3'-TRIIODOTHYRONINE RECEPTOR LIGANDS

[76] Inventors: Ulf Norinder, Nydalavägen 8, Södertälje, Sweden, S-15251; Jurgen Bajorath, 928-137th St. SW., Everett, Wash. 98204; Jay F. Stearns, 1014 Hopper Ave., No. 415, Santa Rosa, Calif. 95403

[21] Appl. No.: 480,643

[22] Filed: Jun. 7, 1995

Related U.S. Application Data

[62] Division of Ser. No. 142,350, filed as PCT/SE92/00307, May 12, 1992, published as WO92/20331, Nov. 26, 1992.

[30] Foreign Application Priority Data

May 17, 1991 [SE] Sweden ................................ 9101509

[51] Int. Cl.⁶ .................... A61K 31/14; A61K 31/055; C07C 211/63; C07C 39/15
[52] U.S. Cl. .................... 514/643; 514/730; 564/283; 568/722
[58] Field of Search ................ 546/283; 568/722; 564/283; 514/643, 730

[56] References Cited

FOREIGN PATENT DOCUMENTS

| A20398326 | 11/1990 | European Pat. Off. . |
| M2280 | 1/1964 | France . |
| A1224490 | 4/1975 | France . |
| A12314711 | 1/1977 | France . |

OTHER PUBLICATIONS

Balani R A, Sethna S (1971). J. Indian Chem Soc. 48(5) 417–22. (abstract).
Balabaskaran S, Smith J N (1970) Biochem J. 117(5) 989–96. (abstract).

Primary Examiner—C. Warren Ivy
Assistant Examiner—Evelyn Huang
Attorney, Agent, or Firm—Darby & Darby

[57] ABSTRACT

Use of a compound selected from the group consisting of 3,5-diiodo-4-(2-N,N-diethylaminoethoxy)phenyl-(2-butyl-benzofur-3-yl)methanol hydrochloride (001), 2-methyl-3-(3,5-diiodo-4-(2-N,N-diethylaminoethoxy)-benzoyl)benzofuran hydrochloride (003), 2-n-butyl-3-(3,5-diiodo-4-carboxymethoxybenzoyl)benzofuran (005), 2-methyl-3-(3,5-diiodo-4-hydroxy-benzoyl)benzofuran (011), 2-methyl-3-(3,5-diiodo-4-carboxymethoxybenzyl)benzofuran (015), 4'-hydroxy-3'-iodo-3,5-diiodo-4-(2-N,N-diethylaminoethoxy)benzophenon hydrochloride (024), 2-butyl-3-(3-iodo-4-hydroxybenzoyl)benzofuran (029), 4'4'-dihydroxy-3'3,5-triiododiphenylmethan (032), which compound is a 3,5,3'-triiodothyronine (T-3) receptor ligand, for the preparation of a medicament for the therapeutic or prophylactic treatment of a disorder which depends on the expression of T-3 regulated genes, and pharmaceutical preparations comprising said compounds, are disclosed. Further, a method of prophylactically or therapeutically treating a patient having a disorder which depends on the expression of 3,5,3"-triiodo-thyronine (T-3) regulated genes is also disclosed. The invention additionally comprises product protection for all the above listed compounds, except the compound (011).

3 Claims, No Drawings

3,5,3'-TRIIODOTHYRONINE RECEPTOR LIGANDS

This is a division of application Ser. No. 08/142,350, filed Feb. 25, 1994, which in turn is a National phase of PCT/SE92/00307 filed May 12, 1992.

The present invention relates to receptor ligands. More specifically it related to the use of 3,5,3'-triiodothyronine (T-3) receptor ligands, and some new T-3 receptor ligands, which are T-3 antagonists.

BACKGROUND

Thyroid hormones have widespread effect on the rate of metabolism and oxygen consumption. They have notably profound effects on the heart, both on the strength and rate of the contractions. Marked changes in cardiac function occur in patients with hyper- or hypothyroidism. Cardiac contractility is increased in the hyperthyroid state and decreased in hypothyroidism and changes in specific proteins accompany these alterations.

The effect of thyroid hormone is mediated through binding of the hormone to thyroid hormone receptors which are nuclear proteins. The ligand-receptor complex binds to specific DNA motifs so called thyroid responsive elements (TRE) located in the promoter region of 3,5,3'-triiodothyronine (T-3) regulated genes. Through interaction with the transcriptional machinery of the cell, composed of ubiquitous and cell specific factors, the expression of the gene is positively or negatively regulated. Examples. of genes of importance for cardiac funtion which are regulated by T-3 are the myosin heavy chains, β adrenergic receptors and Na+K+ATPase.

Amiodarone, which for long has been used in therapy against many types of arrhythmias, acts as a competitive antagonist to thyroid action as defined by its dose dependent ability to [1]compete with T-3 binding to the thyroid hormone receptor and [2]inhibit T-3 induced increase in rat growth hormone (rGH) mRNA levels in cultured rat pituitary cells (Latham et al., J. Am. Coll. Cardiol Vol 9 (1987) pp 872–6; Norman and Lavin, J. Clin. Invest Vol 83 (1989) pp.)

The chemical structures of the T-3 receptor ligands disclosed herein are similar to that of amiodarone. Further, said ligands are T-3 antagonists. Thus, they are useful in the treatment of disorders which depend on the expression of T-3 regulated genes, such as heart arrhythmia and hyperthyroidism.

DESCRIPTION OF THE INVENTION

One aspect of the invention is directed to the use of a compound selected from the group consisting of 3,5-diiodo-4-(2-N,N-diethylaminoethoxy)phenyl-(2-butylbenzofur-3-yl)methanol hydrochloride (001)

2-methyl-3-(3,5-diiodo-4-(2-N,N-diethylaminoethoxy)-benzoyl)benzofuran hydrochloride (003)

2-n-butyl-3-(3,5-diiodo-4-carboxymethoxybenzoyl)benzofuran (005)

2-methyl-3-(3,5-diiodo-4-hydroxy-benzoyl)benzofuran (011)

2-methyl-3-(3,5-diiodo-4-carboxymethoxybenzyl)benzofuran (015)

4'-hydroxy-3'-iodo-3,5 diiodo-4-(2-N,N-dimethylaminoethoxy)benzophenon hydrochloride (024)

2-butyl-3-(3-iodo-4-hydroxybenzoyl)benzofuran (029)

4',4-dihydroxy-3'3,5-triiodo-diphenylmethan (032)
which compound is a 3,5,3'-triiodothyronine (T-3) receptor ligand, for the preparation of a medicament for the therapeutic or prophylactic treatment of a disorder which depends on the expression of T-3 regulated genes.

The above compound (011) has been previously published and e.g. reported (Compt. Rend. 253 (1961) p. 1075–1076; CA 57:10497c) to have spasmolytic activity on isolated intestine of the guinea-pig and some dilatory effects on the coronary vessels of the heart of the rabbit.

Disorders which are believed to be dependent on the expression of T-3 regulated genes are i.a. heart arrhytmia and hyperthroidism. In one embodiment of this aspect of the invention the above listed compounds are used for the treatment of at least one of heart arrhytmia and hyperthyroidism.

Another aspect of the invention is directed to a method of prophylactically of therapeutically treating a patient having a disorder which depends on the expression of 3,5,3'-triiodothyronine (T-3) regulated genes, which method comprises administering to said patient a pharmacologically effective amount of a compound selected from the group consisting of 3,5-diiodo-4-(2-N,N-diethylaminoethoxy)phenyl-(2-butylbenzofur-3-yl)methanol hydrochloride (001)

2-methyl-3-(3,5-diiodo-4-(2-N,N-diethylaminoethoxy)-benzoyl)benzofuran hydrochloride (003)

2-n-butyl-3-(3,5-diiodo-4-carboxymethoxybenzoyl)benzofuran (005)

2-methyl-3-(3,5-diiodo-4-hydroxy-benzoyl)benzofuran (011)

2-methyl-3-(3,5-diiodo-4-carboxymethoxybenzyl)benzofuran (015)

4'-hydroxy-3'-iodo-3,5 diiodo-4-(2-N,N-dimethylaminoethoxy)benzophenon hydrochloride (024)

2-butyl-3-(3-iodo-4-hydroxybenzoyl)benzofuran (029)

4',4-dihydroxy-3'3,5-triiodo-diphenylmethan (032)

In one embodiment of this aspect of the invention the above compounds are used for the treatment of at least one of heart arrhythmia and hyperthyroidism.

Yet another aspect of the invention is directed to a pharmaceutical preparation which comprises, as an active ingredient, a compound selected from the group consisting of 3,5-diiodo-4-(2-N,N-diethylaminoethoxy)phenyl-(2-butylbenzofur-3-yl)methanol hydrochloride (001)

2-methyl-3-(3,5-diiodo-4-(2-N,N-diethylaminoethoxy)-benzoyl)benzofuran hydrochloride (003)

2-n-butyl-3-(3,5-diiodo-4-carboxymethoxybenzoyl)benzofuran (005)

2-methyl-3-(3,5-diiodo-4-hydroxy-benzoyl)benzofuran (011)

2-methyl-3-(3,5-diiodo-4-carboxymethoxybenzyl)benzofuran (015)

4'-hydroxy-3'-iodo-3,5 diiodo-4-(2-N,N-dimethylaminoethoxy)benzophenon hydrochloride (024)

2-butyl-3-(3-iodo-4-hydroxybenzoyl)benzofuran (029)

4',4-dihydroxy-3'3,5-triiodo-diphenylmethan (032)
together with pharmaceutically acceptable additive(s) and/or diluent(s). Suitable additives and/or diluents can be found e.g. in the US Pharmacopoeia, and they will be chosen individually for each specific preparation.

In one embodiment of this aspect of the invention the compound is a 3,5,3'-triiodothyronine receptor ligand.

Still another aspect of the invention is directed to a compound selected from the group consisting of

- 3,5-diiodo-4-(2-N,N-diethylaminoethoxy)phenyl-(2-butylbenzofur-3-yl)methanol hydrochloride (001)
- 2-methyl-3-(3,5-diiodo-4-(2-N,N-diethylaminoethoxy)-benzoyl)benzofuran hydrochloride (003)
- 2-n-butyl-3-(3,5-diiodo-4-carboxymethoxybenzoyl)benzofuran (005)
- 2-methyl-3-(3,5-diiodo-4-carboxymethoxybenzyl)benzofuran (015)
- 4'-hydroxy-3'-iodo-3,5 diiodo-4-(2-N,N-dimethylaminoethoxy)benzophenon hydrochloride (024)
- 2-butyl-3-(3-iodo-4-hydroxybenzoyl)benzofuran (029)
- 4',4-dihydroxy-3'3,5-triiodo-diphenylmethan (032)

In one embodiment of this aspect of the invention the compound is a 3,5,3'-triiodothyronine receptor ligand.

Syntheses

All structures were confirmed by NMR analysis (VARIAN XL-300)

2-methyl-3-(3,5-diiodo-4-hydroxy-benzoyl)benzofuran (011)

(1)

To an ice-cooled solution of 2-methylbenzofuran 1.0 g (7.57 mmol) and p-anisoylchloride 1.3 g (7.62 mmol) in dry dichloromethane 25 ml, stannic chloride 1.0 ml (8.5 mmol) was added dropwise during 5 min with stirring, and the mixture was left for 4 h at room temperature, then poured into a mixture of 100 ml water and 150 ml dichloromethane. The organic layer was washed with 2×50 ml 1M HCl, 2×50 ml 0.5M NaOH, 2×50 ml water and 50 ml saturated NaCl$_{(aq)}$ and dried (MgSO$_4$). Evaporation of the dried dichloromethane gave 1.9 g (95%). This was used directly in the next step.

(2)

A mixture of 2-methyl-3-(4-methoxybenzoyl)benzofuran 1.9 g (7.13 mmol) and pyridinehydrochloride (dry) 4.95 g (42.8 mmol) was gently refluxed for 30 min. When the temperature was below 100° C. 25 ml 1M HCl was added. The precipitated hydroxyketone which solidified over night was dried, which gave 1.8 g (100%).

(3)

A solution of iodine 3.9 g (15.4 mmol) and potassium iodide 3.8 g (22.9 mmol) in water 20 ml, was added dropwise during 15 min to a stirred solution of 2-methyl-3-(4-hydroxybenzoyl)benzofuran 1.8 g (7.13 mmol) in 50 ml 25% ammoniumhydroxide. The mixture was stirred at room temperature for 48 h, acidified with ice-cooled sulphuric acid (15%). The resultant precipitate was collected, washed with water, and dried to give a red solid which was purified on silica to give 3.2 g (89%) (011).

2-n-butyl-3-(3,5-diiodo-4-carboxymethoxy-benzoyl)benzofuran (005)

Steps 1 to 3 are performed in analogy with the steps 1 to 3 of the synthesis of (011)

(4)

A mixture of 2-n-butyl-3-(3,5-diiodo-4-hydroxybenzoyl)benzofuran 1.0 g (1.83 mmol) and potassiumcarbonate 0.56 g (4 mmol) in aceton (dry) 100 ml, α-brom ethylacetate 1.0 g (12 mmol was added, and the solution was extracted with 100 ml water. The organic layer was evaporated to dryness and the yellow rest was dissolved in methanol 50 ml+1M NaOH 50 ml. The solution was heated to 50° C. for 15 h, extracted with 3×75 ml dichloromethane, and dried (MgSO$_4$). Evaporating the solution and purification on silica gave 0.55 g (005).

3,5-diiodo-4-(2-N,N-diethylaminoethoxy)phenyl-(2-butylbenzofur-3-yl)methanol hydrochloride (001)

Steps 1 to 3 are performed in analogy with the steps 1 to 3 of the synthesis of (011)

(4)

To a solution of 2.4 g (4.4 mmol) of 2-butyl-3-(3,5-diiodo-4-hydroxybenzoyl) benzofuran in 10 ml dry toluene was added 3 ml NaOMe (4.4 mmol) in MeOH. After the solution had been stirred for 20 min, 1.1 g (6.6 mmol) of N-2-chloroethyl-N,N-diethylamine, which had been obtained from the hydrochloride, in 5 ml toluene was added. The reaction was refluxed for 15 h. The solution was diluted with 200 ml toluene and extracted with 2×50 ml 1M NaOH, 2×50 ml H$_2$O and 50 ml saturated NaCl$_{(aq)}$. Drying (MgSO$_4$), evaporation of the toluene and purification on silica gave 1.3 (43%).

(5)

2-butyl-3-(3,5-diiodo-4-(2-N,N-diethylaminoethoxy)-benzoyl)benzofuran) 1.0 g (1.5 mmol) was dissolved in abs ethanol 10 ml and sodiumborohydride 0.42 g (11.3 mmol) was added. The mixture was stirred for 15 h at room temperature, CH$_2$Cl$_2$ 100 ml was added and then washed with 2×50 ml H$_2$O and dried (MgSO$_4$), followed by evaporation of the solvent. The residue was acidified with HCl to yield (0.8 g) (80%) (001).

2-methyl-3-(3,5-diiodo-4-(2-N,N-diethylaminoethoxy)-benzoyl)benzofuran hydrochloride (003)

Steps 1 to 3 are performed in analogy with the steps 1 to 3 of the synthesis of (011) Step 4 is performed in analogy with the step 4 of the synthesis of (001)

The residue was acidified with HCl to give (003).

2-methyl-3-(3,5-diiodo-4-carboxymethoxybenzyl)benzofuran (015)

Step 1 is performed in analogy with the step 1 of the synthesis of (011).

(2)

Aluminiumchloride, 1.75 g (13.16 mmol), in 5 ml ether was added to a suspension of lithiumaluminiumhydride, 0.25 g (6.58 mmol), in 3 ml ether during 20 min. 2-methyl-3-(4-methoxybenzoyl)benzofuran, 1.0 g (3.76 mmol), in 10 ml ether was added during 30 min, and the mixture then heated for 45 min. Excess of the reagent was destroyed by adding 0.35 ml H$_2$O, 0.35 ml 1M NaOH and 3 ml H$_2$O to the mixture. Ether, 200 ml, was added, and the organic layer was extracted with 2×100 ml H$_2$O, 2×100 ml 1M sulphuric acid, 100 ml H$_2$O and dried (MgSO$_4$), evaporating gave 0.95 g of 2-methyl-3-(4-methoxybenzyl)benzofuran which was purified on silica.

Steps 3 and 4 are performed in analogy with the steps 2 and 3 of the synthesis of (011) Step 5 is performed in analogy with the step 4 of the synthesis of (005).

4'-hydroxy-3'-iodo-3,5-diiodo-4-(2-N,N-dimethylaminoethoxy)benzophenon hydrochloride (024)

(1)

To a solution of 2.0 g (9.3 mmol) of 4,4'-dihydroxybenzophenon in 50 ml dry acetone was added 27.5 ml of 0.34M NaOMe in MeOH. After the reaction mixture had been stirred for 20 min, 1.6 g (9.3 mmol) of benzylbromide was added. The reaction was stirred at room temperature for 15 h. 250 ml EtOAc was added and then extracted with 2×50 ml 0.5M HCl, 2×50 ml H$_2$O and 50 ml saturated NaCl$_{(aq)}$. Drying (MgSO$_4$), evaporation of the EtOAc and purification on silica gave 0.93 g (33%) of 4'-benzyloxy-4-hydroxy benzophenon.

(2)

A solution of 1.6 g (6.3 mmol) of $I_2$ and 1.6 g (9.6 mmol) KI in 5 ml of $H_2O$, was added dropwise during 10 min to a stirred solution of 0.92 g (3.0 mmol) of 4'-benzyloxy-4-hydroxy benzophenon in 25 ml 25% $NH_3$. The mixture was stirred for 15 h at room temperature, acidified with ice-cooled sulphuric acid (5M) and extracted with 2×100 ml EtOAc. The organic layer was washed with 50 ml $H_2O$, and dried ($MgSO_4$). Evaporation of the EtOAc and purification on silica gave 1.0 g (60%) of 4'-benzyloxy-3,5-diiodo-4-hydroxybensophenon.

(3)

To a solution of 2.0 g (3.6 mmol) of 4'-benzyloxy-3,5-diiodo-4-hydroxybensophenon in 50 ml dry toluene was added 2.3 ml of 1.6 NaOMe in MeOH. After the solution had been stirred for 20 min, 0.58 g (5.4 mmol) of N-2-chloroethyl-N,N-dimethylamine, which had been obtained from the hydrochloride, was added. The reaction was refluxed for 15 h. The solution was diluted with 200 ml toluene and extracted with 2×50 ml 1M NaOH, 2×50 ml $H_2O$ and 50 ml saturated $NaCl_{(aq)}$. Drying ($MgSO_4$), evaporation of the toluene and purification on silica gave 0.96 g (43%) of 4'-benzyloxy-3,5 diiodo-4-(2-N,N-dimethylamino-ethoxy-)benzophenon.

(4)

0.43 g (0.69 mmol) of 4'-benzyloxy-3,5-diiodo-4-(2-N,N-dimetylamino-ethoxy)benzophenon was dissolved in 2.5 ml (5.5 mmol) of $CF_3COOH$ and the solution was stirred at room temperature for 18 h. The mixture was evaporated and the residue was dissolved in 100 ml EtOAc, and was extracted with 50 ml $H_2O$ and 3×50 ml 1M HCl. The acid phases were combined and washed with 50 ml EtOAc and neutralized with 5M NaOH. Extraction with 3×50 ml EtOAc, and drying ($MgSO_4$), gave 0.2 g (54%) of 4'-hydroxy-3,5 diiodo-4-(2-N,N-dimethylamino-ethoxy)benzophenon.

(5)

A solution of 0.24 g (0.93 mmol) of $I_2$ and 0.24 g (1.42 mmol) of KI in 3 ml of $H_2O$, was added dropwise during 10 min to a stirred solution of 0.5 g (0.93 mmol) of 4'-hydroxy-3,5-diiodo-4-(2-N,N-dimethylamino-ethoxy)benzophenon, in 25 ml 25% $NH_3$. The mixture was stirred for 15 h at room temperature, acidified with ice-cooled sulphuric acid (5M), and extracted with 2×100 ml EtOAc. The organic layer was washed with 50 ml $H_2O$, dried ($MgSO_4$) and the EtOAc was removed at reduced pressure to give 0.6 g of 4'-hydroxy-3'-iodo-3,5-diiodo-4-(2-N,N-dimethylamino-ethoxy)benzophenon. The residue was acidified with HCl to give (024).

2-butyl-3-(3-iodo-4-hydroxybenzoyl)benzofuran (029)

Steps 1 to 3 are performed in analogy with the steps 1 to 3 of the synthesis of (011)

4',4-dihydroxy-3'3,5-triiodo-diphenylmethan (032)

(1)

To a solution of 2.0 g (10 mmol) of 4,4'dihydroxyphenylmethan in 100 ml dry acetone was added 29.4 ml of 0.34M NaOMe in MeOH. After the reaction mixture had been stirred for 20 min 1.7 g (10 mmol) of benzylbromide was added. The reaction was stirred at room temperature for 15 h. 250 ml EtOAc was added and then extracted with 2×50 ml 0.5M HCl, 2×50 ml $H_2O$ and 50 ml saturated $NaCl_{(aq)}$. Drying ($MgSO_4$), evaporation of the EtOAc and purification on silica gave 0.9 g (31%) of 4'-benzyloxy-4-hydroxydiphenyl methan.

(2)

A solution of 1.7 g (6.8 mmol) of $I_2$ and 1.8 g (10.8 mmol) of KI in 3 ml of $H_2O$, was added dropwise during 10 min to a stirred solution of 0.9 g (3.1 mmol) of 4'-benzyloxy-4-hydroxy diphenylmethan in 10 ml 25% $NH_3$ and 25 ml 1,4-dioxan. The mixture was stirred for 15 h at room temperature, acidified with ice-cooled sulphuric acid (5M) and extracted with 2×100 ml EtOAc. The organic layer was washed with 50 ml $H_2O$, and dried ($MgSO_4$). Evaporation of the EtOAc and purification on silica gave 1.15 g (68%) of 4'-benzyloxy-3,5-diiodo-4-hydroxydiphenyl methan.

(3)

To a mixture of 0.27 g (0.5 mmol) of 4'-benzyloxy-3,5-diiodo-4-hydroxydiphenyl methan, 1 ml EtSH and 1 ml $CH_2Cl_2$ was added 0.5 ml (4 mmol) $BF_3$-$Et_2O$. The mixture was stirred for 1,5 h, then poured into 25 ml $H_2O$ and extracted with 2×50 ml EtOAc. The EtOAc was washed with 50 ml saturated $NaCl_{(aq)}$, drying ($MgSO_4$), evaporation of the solvent and purification on silica gave 0.22 g of 4'-hydroxy-3,5-diiodo-4-hydroxydiphenyl methan.

(4)

A solution of 0.28 g (1.1 mmol) of $I_2$ and 0.30 g (1.8 mmol) KI in 1 ml of $H_2O$, was added dropwise during 10 min to a stirred solution of 0.5 g (1.1 mmol) of 4'-hydroxy-3,5-diiodo-4-hydroxydiphenyl methan, in 3 ml 25% $NH_3$ and 5 ml 1,4-dioxan. The mixture was stirred for 15 h at room temperature, acidified with ice-cooled sulphuric acid (5M), and extracted with 2×100 ml EtOAc. The organic layer was washed with 50 ml $H_2O$, dried ($MgSO_4$) and the EtOAc was removed at reduced pressure to give, after purification on silica, 0.16 g (25%) of 4'-hydroxy-3'-iodo-3,5 diiodo-4-hydroxydiphenyl methan (032).

Binding experiments

Human thyroid hormone receptor β1 (hThR β1) was expressed in insect cells using a recombinant baculovirus (Barkhem T., et al. The Journal of Steroid Biochemistry and Molecular Biology: Vol 38, No 6 (1991) pp 667-).

The binding assay was performed according to Apriletti (Aprilleti J., et al. The Journal of Biological Chemistry: Vol. 263, No 19, (1988) pp 9409–9417) as described below. hThR β1 was incubated with radioactive labeled 3,5,3'-triiodothyronine ($^{125}$I-T-3) from New England Nuclear (# NEX 110 X, 2200 Ci/mmol) in the presence of a range of concentrations of the compound ((011)) or amiodarone.

Solutions of hThR β1 and of $^{125}$I-T-3 were made in E400 ($K_2HPO_4$=20 mM, KCl=400 mM, $MgCl_2$=1 mM, EDTA= 0,5 mM, monothioglycerol=6 mM, glycerol 8,7% (v/v), histones (type 11AS) 10 µg/ml pH=7,5). Histones and Monothioglycerol were purchased from Sigma (St Louis, Mo., USA), the other compounds in E400 were from Merck (Darmstadt, BRD). Stock solutions (20 mM) in amiodarone were made in 50% EtOH/1 mM HCl. Stock solutions of the compound (011) (20 mM) was made in 5% EtOH/1 mM NaOH.

The stock solution of amiodarone was diluted in 1 mM HCl/5% EtOH and the stock solution of the compound (011) was diluted in 1 mM NaOH/5% EtOH. To 25 µl diluted amiodarone or compound (011), 75 µl $^{125}$I-T-3 in E400 (to final concentration of 200 pMolar) and 100 µl hThR β1 in E400 (to a final concentration of 50 pM) was added.

Addition of 25 µl of NaOH (1 mM)/EtOH (5%) of HCl (1 mM)/EtOH (5%) to 175 µl of buffer do not interfere with the ability of hThR β1 to bind $^{125}$I-T-3 as compared to incubations in E400 alone.

The mixture of hThR β1, $^{125}$I-T-3 and compound (011)/ amiodarone was incubated until reaching binding equilibrium (time>10 h). For convenience the incubations were performed over night (16–20 hours).

The incubation was stopped by the loading of 180 μl incubation mixture on a Quik-Sep Sephadex G-25 column (#9041-35-4 ISOLAB, Akron, Ohio, USA). The peak of protein-bound $^{125}$I-T-3 was eluted with 1 ml E400 and collected in a test tube (passage of free T-3 through column is delayed). The eluted radioactivity was measured in a gamma-counter.

All incubations and dilutions were made in polypropylene tubes. Great care was taken to avoid exposure of hThR β1 to temperatures above +4° C.

The eluted radioactivity was plotted against the logarithmic concentration of the compound ((011)) or amiodarone and fitted to the equation $6=((m1-m4)/(1+m0/m3)^{m2})+m4$ were m1=maximum binding level (binding in absence of inhibitor), m4=minimum binding level (binding in presence of infinite concentration of inhibitor), m3=the concentration of inhibitor that reduces binding to 50% of maximum binding level (IC-50-value), m4=the slope of curve at m3. (DeLean, A., et al, Am. J. Physiol. 235: E97–E102. (1978)).

The calculations were performed in KaleidaGraph™ 2.0.2 (Adelbeck Software) on a Macintoxh IIcx computer.

The m3-values (IC-50) were used to define the binding affinity of compounds (here amiodarone and the compound (011)) that bind to hThR β1.

The above binding experiment was repeated with the compounds of the invention, and the following results were obtained Experiments conducted with $[hThR\beta]=5.0\times10^{-11}M$ and with $[^{125}I\text{-}T_3]=2.0\times10^{-10}M$

| Substance | IC-50 (Molar) |
| --- | --- |
| 3,5-diiodo-4-(2-N,N-diethylaminoethoxy)-phenyl-(2-butylbenzofur-3-yl)methanol hydrochloride | (001) 3.6 × 10$^{-6}$ |
| 2-methyl-3-(3,5-diiodo-4-(2-N,N-diethylaminoethoxy)-benzoyl)benzofuran hydrochloride | (003) 10 × 10$^{-6}$ |
| 2-n-butyl-3-(3,5-diiodo-4-carboxymethoxy-benzoyl)benzofuran | (005) 4.0 × 10$^{-6}$ |
| 2-methyl-3-(3,5-diiodo-4-hydroxy-benzoyl)benzofuran | (011) 2.5 × 10$^{-6}$ |
| 2-methyl-3-(3,5-diiodo-4-carboxymethoxy-benzyl)benzofuran | (015) 8.0 × 10$^{-6}$ |
| 4'-hydroxy-3'-iodo-3,5 diiodo-4-(2-N,N-dimethylamino-ethoxy)benzophenon hydrochloride | (024) 1.1 × 10$^{-5}$ |
| 2-butyl-3-(3-iodo-4-hydroxybenzoyl)benzofuran | (029) 3.2 × 10$^{-6}$ |
| 4',4-dihydroxy-3'3,5-triiodo-diphenylmethan | (032) 4.2 × 10$^{-7}$ |

By using a biological assay, such as the method of Westerfield et al. (Endocrinology: Vol. 77, (1965) pp 802) all the compounds (001), (003), (005), (011), (015), (024), (029) and (032) can be shown to be T-3 receptor antagonists.

LIST OF COMPOUNDS

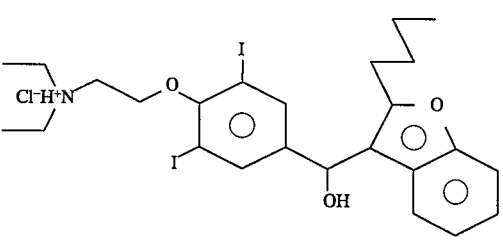
(001)

-continued
LIST OF COMPOUNDS

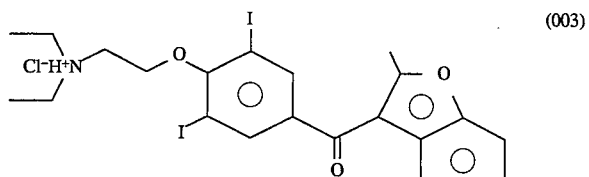
(003)

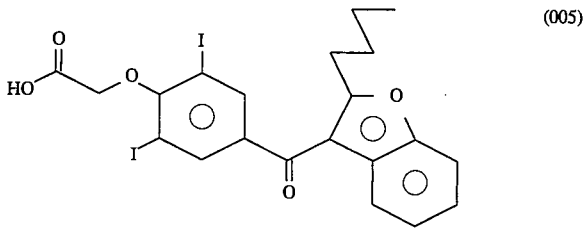
(005)

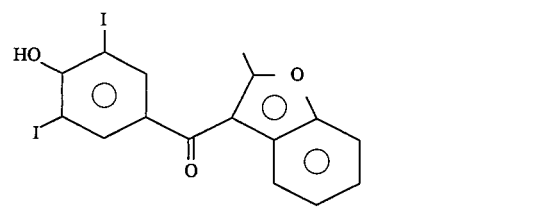
(011)

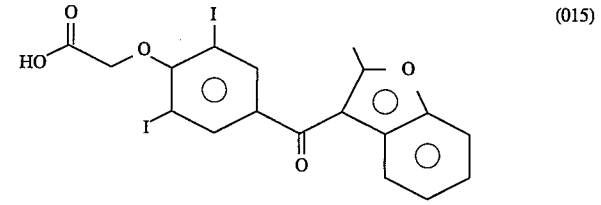
(015)

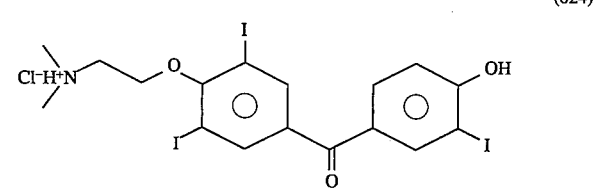
(024)

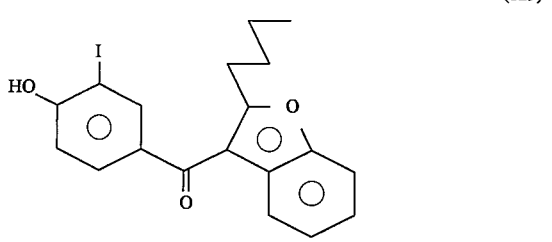
(029)

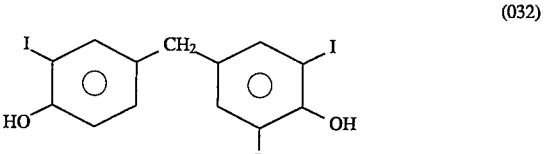
(032)

-continued
LIST OF COMPOUNDS

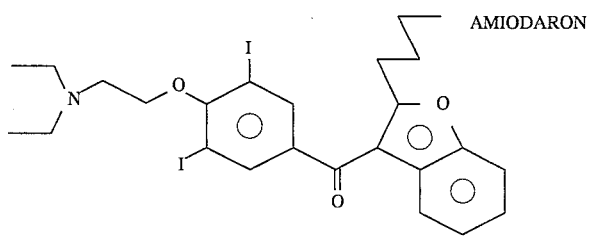
AMIODARON

We claim:

1. A method for preventing or treating cardiac arrhythmia, which method comprises administering to said patient an amount effective to treat said arrhythmia of a compound selected from the group consisting of 4'-hydroxy-3'-iodo-3,5 diiodo-4-(2-N,N-dimethylamino-ethoxy)benzophenon hydrochloride and 4',4-dihydroxy-3'3,5-triiodo-diphenylmethan.

2. A pharmaceutical preparation comprising, as an active ingredient, a 3,5,3' triiodothyronine receptor ligand selected from the group consisting of 4'-hydroxy-3'-iodo-3,5 diiodo-4-(2-N,N-dimethylamino-ethoxy)benzophenon hydrochloride and 4',4-dihydroxy-3'3,5-triiodo-diphenylmethan;

together with a pharmaceutically acceptable carrier or diluent.

3. A 3,5,3'triiodothyronine receptor ligand selected from the group consisting of 4'-hydroxy-3'-iodo-3,5 diiodo-4-(2-N,N-dimethylamino-ethoxy)benzophenon hydrochloride and 4',4-dihydroxy-3'3,5-triiodo-diphenylmethan.

* * * * *